United States Patent
Carswell

[19]

[11] Patent Number: 5,812,234
[45] Date of Patent: Sep. 22, 1998

[54] PROTECTIVE EYEGLASS CONSTRUCTION WITH RATCHET MECHANISM FOR TILT LENS

[75] Inventor: Craig R. Carswell, Arlington, Mass.

[73] Assignee: Encon Safety Products, Houston, Tex.

[21] Appl. No.: 734,870

[22] Filed: Oct. 22, 1996

[51] Int. Cl.$^6$ .................................................. G02C 5/14
[52] U.S. Cl. ................................... 351/120; 351/118
[58] Field of Search .................................. 351/111, 113, 351/114, 118, 119, 120, 121, 153; 16/228

[56] References Cited

U.S. PATENT DOCUMENTS

| | | | |
|---|---|---|---|
| 3,133,141 | 5/1964 | Anderson | 88/52 |
| 3,394,980 | 7/1968 | Dym | 351/41 |
| 3,556,644 | 1/1971 | Stahl | 351/118 |
| 3,649,107 | 3/1972 | Hoffmaster et al. | 351/118 |
| 3,667,834 | 6/1972 | Davison et al. | 351/118 |
| 3,846,018 | 11/1974 | Gerson | 351/120 |
| 4,153,348 | 5/1979 | Walters et al. | 351/118 |
| 4,527,291 | 7/1985 | Nussbickl | 2/450 |
| 4,991,952 | 2/1991 | Grau | 351/120 |
| 5,257,050 | 10/1993 | Wiedner | 351/86 |
| 5,357,292 | 10/1994 | Wiedner | 351/105 |
| 5,381,192 | 1/1995 | Canavan et al. | 351/118 |
| 5,457,505 | 10/1995 | Canavan et al. | 351/120 |
| 5,555,037 | 9/1996 | Canavan | 351/118 |

FOREIGN PATENT DOCUMENTS

| | | | |
|---|---|---|---|
| 1121534 | 7/1968 | United Kingdom | 351/120 |

OTHER PUBLICATIONS

*Protective Eye Wear;* Catalogue, Jun. 15, 1996 [OTOS].

*Primary Examiner*—Huy Mai
*Attorney, Agent, or Firm*—Jenkens & Gilchrist, P.C.

[57] ABSTRACT

An improved eyeglass construction is described having a novel means for varying the inclination of the lens relative to the temples and for adjusting the length of the temples, which involves an enclosed pair of mating ribbed arcuate segments for adjusting the temples relative to the lens.

8 Claims, 3 Drawing Sheets

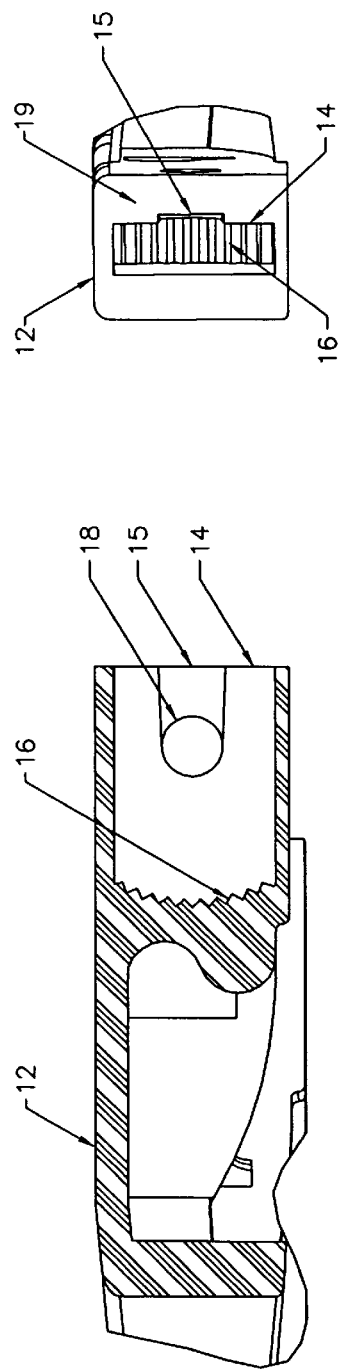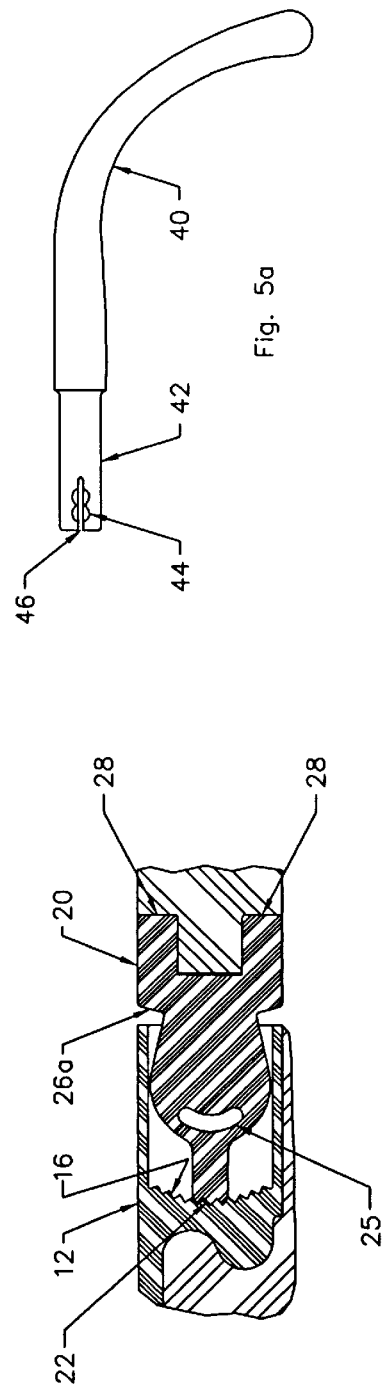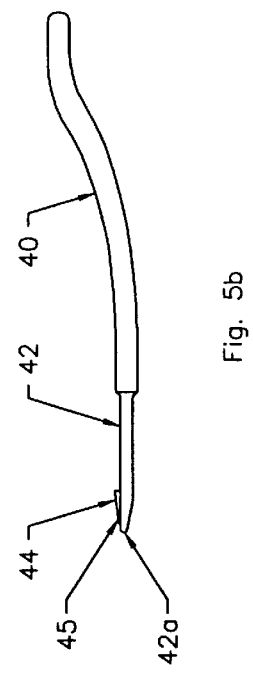

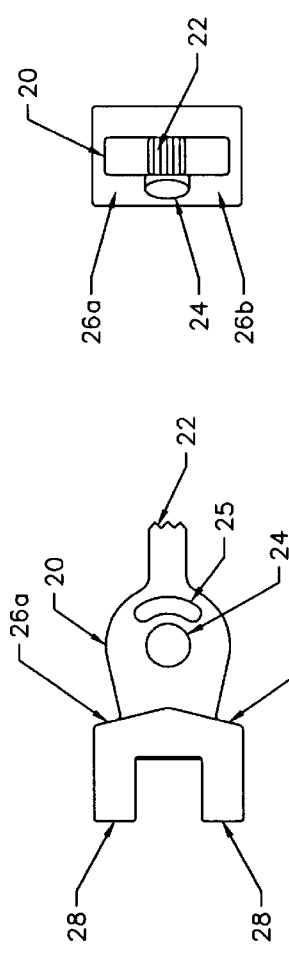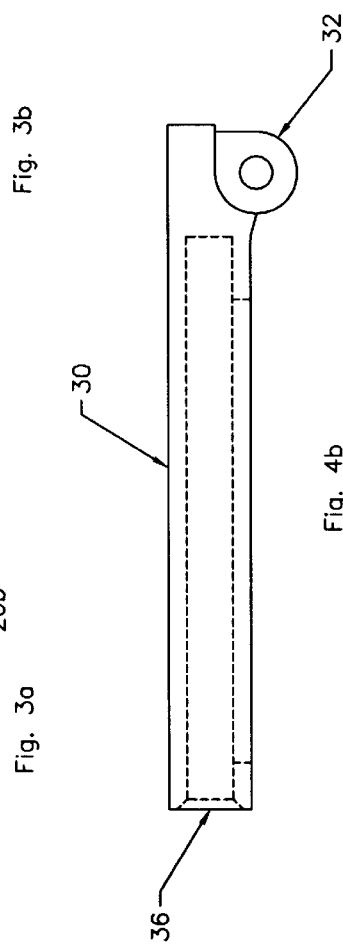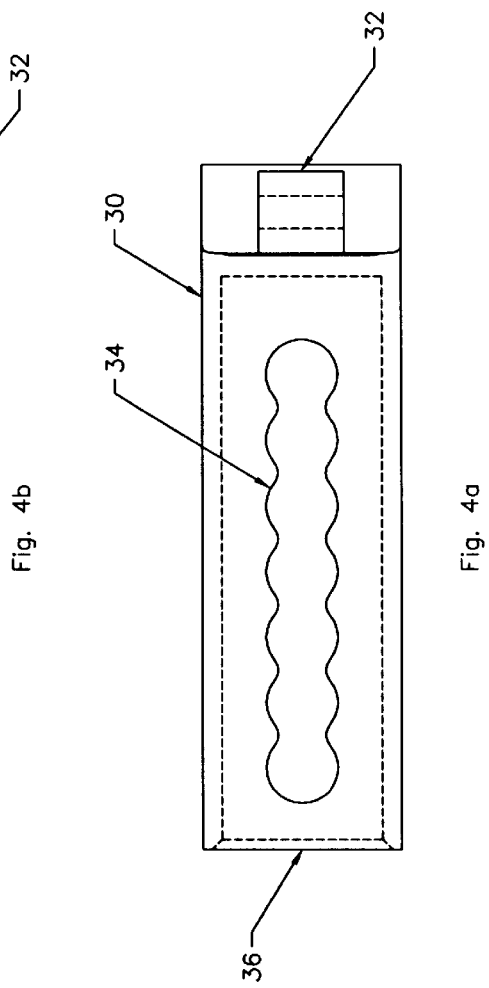

PROTECTIVE EYEGLASS CONSTRUCTION WITH RATCHET MECHANISM FOR TILT LENS

BACKGROUND OF THE INVENTION

1. Field of the Invention

This invention relates generally to an improved construction for protective eyeglasses for use in sport or at work providing variable length temples and adjustment of the angle between the temples and the lens of the spectacles with the added feature that the mating ribbed surfaces for adjustment are concealed from view by the improved way in which the eyeglasses are constructed.

2. Description of the Prior Art

Protective eyeglasses have long been useful in the workplace and in active sports. Often when protection against the glare or the sun is required, the lens of the protective glasses could be suitably tinted and the glasses of this invention are particularly attractive that could be worn as fashionable sunglass eyewear. Protective eyeglasses, having adjustable length temples and angular adjustment between the temples and the lens are well known. There are many configurations of the apparatus which are used to impart these features to the eyeglass. Often the mechanism to perform such flexibility of the eyeglasses results in relatively unattractive and unsightly protective eyeglasses, thus diminishing the interest in wearing them on the job or as fashionable accessories. For instance, the following U.S. Pat. Nos. describe protective eyeglasses which have both variable length temples and angular adjustment between the temples and the lens: 5,381,192; 5,555,037; 5,457,505; 5,357,292; 5,257,050; 4,527,291; and 4,991,952. U.S. Pat. No. 3,846,018 describes eyeglasses which provide for the angular adjustment of the lens vis a vis the temple. With the exception of this last mentioned patent, the prior art listed above also describes a mechanism for lengthening the temples. In addition, U.S. Pat. Nos. 4,153,348; 3,667,834; 3,394,980; and 3,133,141 also describe adjustable temples for eyeglasses.

The characteristic of the foregoing patents with respect to the pivotal movement of the temple relative to the plane of the lens is that in each case the mechanism is clearly visible to others in the vicinity of the wearer. Likewise, the liability and wearability of the described systems have periodically been brought into question.

It is, accordingly, an object of this invention to provide the adjustability of the angular relationship between the temple and the lens in an unobtrusive, if not invisible, and reliable manner.

It is a further object of this invention to provide protective eyeglasses having variable length temples and an adjustment between the temples and the lens which is easily and efficiently manufactured and assembled.

SUMMARY OF THE INVENTION

The protective eyeglasses of this invention are an improved construction of protective eyeglasses for work or sports environment, whether tinted or not, as sunglasses, normally have a frame portion holding a lens piece and held on the head by a pair of temples attached to the frame. The embodiments improved by this invention also normally include a means to vary the length of the temples, as well to adjust the inclination between the temples and the lens. It is accomplished in the present invention through a transition piece called a pivot piece which is plugged into a rearward facing tubular portion on each end of the frame. One end of the pivot piece carries part of the hinge for attaching the temples while the other end is a forward facing ribbed arcuate segment having a detent forming a horizontal axis at the center of radius. The rearward facing tubular portion of the frame encloses a ribbed arcuate segment, oriented about a horizontal axis, having substantially the same radius as the forward facing ribbed arcuate segment such that upon insertion of the pivot piece into the rearward facing tubular portion, the ribs of the arcuate segment of the pivot piece engage the ribs of the rearward facing segment with the detent, or post, at the center of the radius of the pivot piece being carried by a depression, or hole, at the center of radius in the rearward facing tubular portion. The inclination angle between the temples and the lens thus may be changed by repositioning the ribbed arcuate segments against each other about the horizontal center axis defined by the hole and center post.

The temples themselves are variable in length through the use of a fixed front and telescoping rear portions. The front portion is, at least in part, of tubular construction having a series of inter connected holes forming serrated slots adapted to receive a means for holding the temples at a desired length in the form of a nub, detent or post. The serrated slots are engaged preferably by longitudinally based nubs which are moved from slot to slot or by segmented cylindrical posts mounted on each side of a resilient spring which flexes when the cylindrical posts are moved from one slot to the other.

The improved eyeglasses of this invention allow for the inclination to be adjusted without resorting to the use of unattractive external mechanisms which may also be damaged because of the openness of the condition.

DESCRIPTION OF THE DRAWINGS

In considering the following description of this invention, reference may be made to the attached drawings herein described for purposes of assistance in clarity, rather than limitation of the claims of the above-identified application:

FIG. 2A is an end view looking forward toward the rearward facing tubular portion of the frame.

FIG. 2B is a section view of the rearward facing tubular portion of the frame showing the rear facing arcuate ribbed segment.

FIG. 3A shows the outside elevation drawing of the pivot piece depicting the center post.

FIG. 3B shows the end view of the pivot piece toward the ribbed arcuate segment which, when assembled, faces forward in the eyeglasses.

FIG. 3C shows, partly in section, the pivot piece in position within the tubular portion of the frame showing the arcuate ribbed segments in meshed configuration.

FIG. 4A is an elevation view of the inside of the front tubular portion of the telescoping temples showing the connected series of slots.

FIG. 4B is a top view of the front portion section.

FIG. 5A is a side view of the rear portion of the telescoping section.

FIG. 5B is a top view of one of the rear portions of the telescoping temples.

Figure 1:
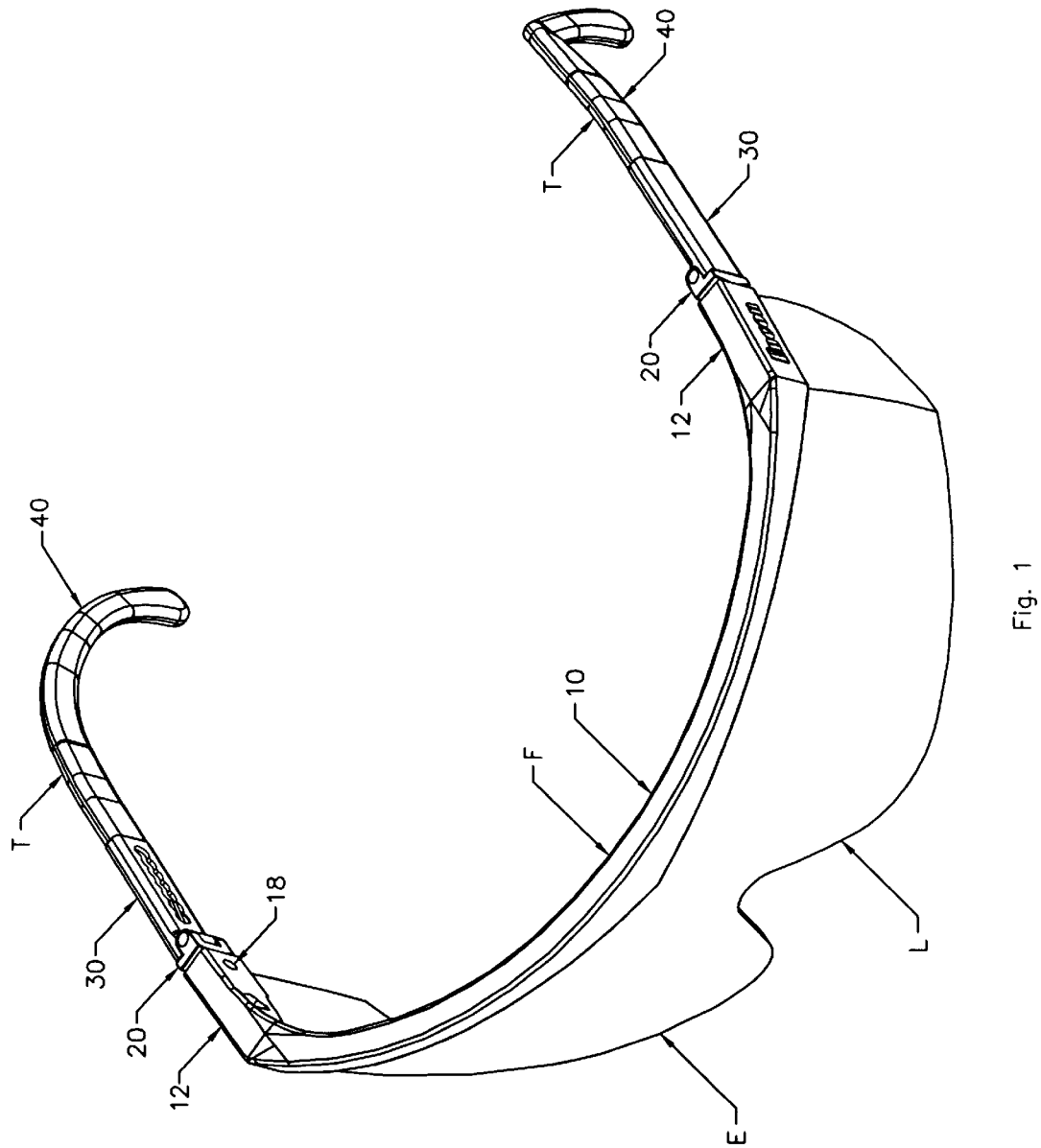
FIG. 1 is a perspective view of one embodiment of the eyeglasses of the invention described herein.

It is to be understood that these drawings illustrate only typical embodiments of the invention and are not to be construed to be limiting to the scope because other equally effective embodiments may be appropriate.

DETAILED DESCRIPTION OF THE INVENTION

The protective eyeglass construction of this invention is an improvement over prior constructions having the features of variable length temples and adjustable inclination of the lens relative to the temples of the eyeglass. As seen in FIG. 1, the eyeglasses E of this invention are basically made up of a lens L, a frame F, and temples T. The frame F, generally denominated by the number 10, extends the width of the lens L, either as a single piece or multiple pieces, shown as a single piece 10, having rearward facing tubular portion 12, which is joined to the temples T through a pivot piece 20. The temples T are made up of a generally tubular front portion 30 and a telescoping rear portion 40 which operate together to telescope, allowing the length of the temples to be varied in accordance with the desires of the wearer. The assembled orientation of these major parts is shown in FIG. 1. It is to be understood that the lens L may properly be of a single piece construction or a multiple piece construction and to be either tinted or clear or impact resistant for use as safety glasses or tinted for wear as sunglasses or sports glasses. The lens L of the eyeglass E of this invention may be suitably constructed from any transparent lens material, with polycarbonate being preferred, such as for example, methylmethacrolate, cellulose proprianate, cellulose acetate or cellulose butylate, for example. The lens L may be attached to the frame F in any of the normal ways known to those skilled in the art and does not constitute part of this invention. The sole criteria for the practice of this invention is that the left and right tubular portions 12 be of the described construction to receive the pivot piece 20 in order that the lens plane may be inclined relative the temples.

FIGS. 2A and 2B more specifically disclose the rearward facing tubular portion 12 of frame 10. The end view in FIG. 2A of the end portion 12 so shows a generally rectangular aperture 14 and a ribbed arcuate segment 16, better seen in the sectioned FIG. 2B. The arcuate segment 16 is centered in the rearward facing tubular portion 12 of frame 10 on depression or hole 18 placing a horizontal axis for the radius of curvature. The generally rectangular opening 14 in the rearward facing tubular portion 12 of frame 10 is adapted to receive the pivot piece 20 depicted in FIGS. 3A and 3B. FIG. 3A shows the elevation of the side of the pivot piece 20 which faces inward toward the head when the eyeglasses E are being worn. The pivot piece 20 includes an arcuate segment 22 having substantially the same radius as the arcuate segment 16 of the tubular portion 12 of the frame 10. The center of arcuate segment 22, which would face forward when the glasses E are assembled and worn, have their center in a detent or post 24 which is adapted to protrude through hole 18 in the tubular portion 12. As shown on FIG. 3B, the post 24 is canted downward in the direction of the arcuate segment 22 so that during assembly it would be more easily fit in rectangular opening 14 and contact inclined surface 15 until it reaches the center hole 18 by displacing the plastic material of which the frame F is constructed. Once the center post 24 slides into hole 18, allowing the generally rectangular opening 14 to return to its normal shape, the pivot piece 20 and the frame 10 are assembled such that the rearward facing ribbed arcuate segment 16 and the forward facing ribbed arcuate segment 22 are meshing together, as seen in FIG. 3C. As the pivot piece 20 is pivoted about the center post 24, positioned in access hole 18, the ribs of the arcuate segments operate against each other to secure the angle of inclination between the temple and the lens. This angle may be changed by moving the segment on the pivot piece. This movement is facilitated to reduce the wear on the ribs of arcuate surfaces 16 and 22 by a slot 25 on the pivot piece 20 adjacent the ribbed segment shown best on FIG. 3A. This slot 25 allows the arcuate segment 22 to flex as it moves from rib to rib on rearward facing arcuate segment 16. The pivot piece 20 is limited in rotation by surfaces 26a and 26b which abut against the rear surface 19 of the rearward facing tubular portion 12 of frame 10.

On the rearward portion of pivot piece 20 is the hinge segment 28 which are used in a normal manner, usually with a pin, to connect to the temples T to allow movement about a vertical axis. If desired, this portion of the pivot piece 20 and the temples T could be molded together in what is known as a living hinge which is described, for example, in U.S. Pat. No. 5,528,320, which is incorporated herein by reference for all purposes. The front portion 30 of the temples T is, at least in part, a generally tubular construction having the mating hinge piece 32 for attachment to the hinge pieces 28 of the pivot piece shown in FIGS. 3.

The temple is assembled by inserting the rear portion 40, which is supported by the ear of the wearer, into the tubular front portion 30 which is of generally tubular or rectangular construction to receive the blade 42 of the rear portion 40. The tubular portion 30 is characterized by a series of serrated slots 34, preferably facing inward toward the head of the wearer to receive detents 44 oriented on blade 42 of the rear portion 40. The serrated slots 34 are longitudinally oriented to correspond to the position of the detents 44. When the blade 42 is inserted into the rectangular opening of tubular portion 30 the material of construction is distorted somewhat and the inclined surface 45 of the detents 44 sloping toward the forward edge 42a improve the ease with which the blade 42 is inserted into the rear facing rectangular opening 36 of tubular portion 30. The blade 42 is shown on FIG. 5A having a slot 46 to allow the material of construction to flex to allow movement parts of the detents 44 to move toward each other as they move from one expanded portion of the serrated slots 34 to another. It is preferred to have a plurality of detents 44 in the adjustable portion 40 of the temples T. It is understood that rather than a slot 46 allowing the width of the detents to be varied, slightly rounded nubs could be used to displace the material in narrow areas of the serrated slots 34 providing the means for movement and securing the rear portion 40 of temples T within the tubular portion 30.

Since the materials of the frame F, pivot piece 20 and temples T must flex somewhat in the assembly and adjustment of the improved eyeglass construction of this invention, the selection of the material for these pieces would be a tough flexible plastic material such as, for example, nylon, polyethylene, polypropylene, polyethylene/polyvinyl acetate copolymers and the like. Some polymers are better than others for this purpose and those skilled in the art will be able to make the proper selection. The preferred material for the practice of the present invention is the ST-801 grade of nylon (DuPont, Wilmington, Del.) In the assembly of the eyeglasses, the pivot piece 20 and the front portion 30 of temples T are joined together in the manner to create a hinge for the movement of the temples from an open and a closed position. The rear portion 40, or spatula, of the temples T, can then be inserted into the rectangular opening of the rear tubular portion 30 of temples T until the detent 44 engages the serrated slot 34 to be secured at the proper length for the wearer. Then the ribbed arcuate segment of the pivot piece 20 would be inserted into the rectangular opening 14 of the rearward facing tubular portion 12 of frame 10 along the inclined path 15 until the center post 24 snaps into place in center hole 18, thus allowing the ribbed segment 22 to engage the rearward facing ribbed segment 16. Thus, the improved eyeglasses of this invention are securely assembled.

As a further embodiment of this invention, the position of the tubular portion and the pivot piece could be reversed with the pivot piece and post being attached to either end of the frame and the tubular portion enclosing a forward facing ribbed arcuate segment which engages the pivot piece center post as described above.

From the description of the embodiment set forth above and the affixed drawings, one skilled in the art could make many modifications and variations of the improved protectable eyeglasses of this invention without departing from the spirit and scope of the instantly claimed invention.

I claim:

1. In a protective eyeglass construction comprising a frame portion, including a lens piece, and a pair of temples, attached to the frame portion in a manner to allow the temples to be moved between an opened and closed position, and adjustable in inclination, relative the lens piece, and longitudinally adjustable to different lengths, the improvement which comprises a rearward facing tubular portion on each end of the frame portion, the interior of each such tubular portion having a rearwardly facing, ribbed arcuate segment oriented longitudinally along the tubular portion and vertically relative to the lens piece, and a depression oriented at the center of the radius of the arcuate segment; a pivot piece adapted to be received in the tubular portion, the pivot piece having a forward facing ribbed arcuate surface of substantially the same radius as the rearwardly facing segment within the tubular portion, a post oriented at the center of the radius of the arcuate segments, and a rearward facing hinge portion for attaching the temples in a pivoting relationship about a vertical axis to allow movement between the opened and the closed position; whereby, when the pivot piece is inserted into the tubular portion the ribbed arcuate segments mesh and the post is carried by the depression such that the angle of inclination of the lens piece relative the temples can be changed by rotation of the temples about the horizontal axis defined by the post.

2. The protective eyeglass construction of claim 1 wherein the temples have telescoping front and rear portions, the front portion being of a least part tubular construction having a series of longitudinally placed positioning serrated slots therein, said rear portion having a detent along one edge thereof which is receivable in the positioning serrated slots in the front portion for adjustably securing the relative positions of the front and rear portions, each of said rear portions having a means adjacent the detent defining a resilient spring to allow the detent to flex when moved from one slot to another in the front portion.

3. The protective eyeglass construction of claim 2 wherein the positioning serrated slots are connected by a path through which the detent may traverse and the detent on the rear portion is divided by a slit which allows the detent to move from one positioning serrated slot to another and resiliently spring into the slot to secure the length of the temples.

4. The protective eyeglass construction of claim 2 wherein the rear portion has a slot positioned adjacent to the detent which allows the detent to be deflected slightly when the temples are lengthened or shortened.

5. In a protective eyeglass construction comprising a frame portion, including a lens piece, and a pair of temples, attached to the frame portion in a manner to allow the temples to be moved between an opened and closed position, and adjustable in inclination, relative the lens piece, the improvement which comprises a rearward facing tubular portion at each end of the frame portion, the interior of each such tubular portion having a rearwardly facing, ribbed arcuate segment oriented longitudinally along the tubular portion and vertically relative to the lens piece, and a depression oriented at the center of the radius of the arcuate segment; a pivot piece adapted to be received in the tubular portion, the pivot piece having a forward facing ribbed arcuate surface of substantially the same radius as the rearwardly facing segment within the tubular portion, a post oriented at the center of the radius of the arcuate segments; whereby, when the pivot piece is inserted into the tubular portion the ribbed arcuate segments mesh and the post is carried by the depression such that the angle of inclination of the lens piece relative the temples can be changed by rotation of the temples about the horizontal axis defined by the post.

6. In a protective eyeglass construction comprising a frame portion, including a lens piece, and a pair of temples, attached to the frame portion in a manner to allow the temples to be moved between an opened and closed position, and adjustable in inclination, relative the lens piece, the improvement which comprises a rearward facing pivot piece on each end of the frame portion having a rearward facing ribbed arcuate surface of substantially the same radius as a forward facing ribbed arcuate segment within a tubular portion, a post oriented at the center of the radius of the arcuate segment; a tubular portion adapted to receive the pivot piece arcuate ribbed segment, the interior of each such tubular portion having a forward facing ribbed arcuate segment oriented longitudinally along the tubular portion and vertically relative to the lens piece, and a depression oriented at the center of the radius of the arcuate segment to receive the post of the pivot piece and a rearward facing hinge portion for attaching the temples in a pivoting relationship about a vertical axis to allow movement between the opened and the closed position a rearward facing pivot piece at each end of the frame portion having a rearward facing ribbed arcuate surface of substantially the same radius as a forward facing segment within; whereby, when the pivot piece is inserted into the tubular portion the ribbed arcuate segments mesh and the post is carried by the depression such that the angle of inclination of the lens piece relative the temples can be changed by rotation of the temples about the horizontal axis defined by the post.

7. A pair of eyeglasses having a frame portion, a lens piece, a pair of temples, attached to the frame portion in a manner to allow the temples to be moved between an opened and closed position, and an improvement which comprises:

means for adjusting the inclination of the temples, relative to the lens piece, wherein the adjustment means comprises a pivot piece receiving portion at each end of the frame portion, the pivot piece receiving portion having a ribbed arcuate segment oriented longitudinally along the pivot piece receiving portion and vertically relative to the lens piece; a pivot piece adapted to be received by the pivot receiving portion, the pivot piece having a ribbed arcuate surface of substantially the same radius as the arcuate segment of the pivot piece receiving portion; means for pivotally engaging the ribbed arcuate segment of the pivot receiving portion with the ribbed arcuate segment of the pivot piece at the center of the radius of the arcuate segments; and an end portion; whereby, when the pivot piece receiving portion is pivotally engaged with the pivot piece, the ribbed arcuate segments mesh.

8. The pair of eyeglasses of claim 7, wherein the pivot receiving portion having a depression oriented at the center of the radius of the arcuate segment, having the arcuate segment rearwardly facing relative to the lens piece, and having the covering portion integrally attached to the pivot receiving portion; and the pivot piece having a post oriented at the center of the radius of the arcuate segment of the pivot piece and having the arcuate segment forwardly facing relative to the lens piece; whereby, when the pivot piece receiving portion is joined with the pivot piece, the post is seated in the depression.

* * * * *